United States Patent
Lettmann et al.

(12)

(10) Patent No.: US 6,924,385 B2
(45) Date of Patent: Aug. 2, 2005

(54) METHOD FOR SYNTHESIS OF ALIPHATIC ISOCYANATES FROM AROMATIC ISOCYANATES

(75) Inventors: Christian Lettmann, Coesfeld (DE); Stephan Kohlstruk, Duelmen (DE); Guido Stochniol, Gelnhausen (DE); Emmanouil Spyrou, Marl (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/331,555

(22) Filed: Dec. 31, 2002

(65) Prior Publication Data

US 2004/0097752 A1 May 20, 2004

(30) Foreign Application Priority Data

Nov. 18, 2002 (DE) .......................................... 102 53 803

(51) Int. Cl.[7] ....................... C07C 263/02; C07C 209/10
(52) U.S. Cl. ....................... 558/302; 564/450; 564/451
(58) Field of Search ......................... 558/302; 564/450, 564/451

(56) References Cited

U.S. PATENT DOCUMENTS 5,936,126 A * 8/1999 Ruhl et al. ................... 564/451

FOREIGN PATENT DOCUMENTS

| DE | 44 07 019  | 9/1994  |
|----|------------|---------|
| EP | 0 023 649  | 2/1981  |
| EP | 0 324 190  | 7/1989  |
| EP | 0 813 906  | 12/1997 |
| EP | 0 814 098  | 12/1997 |
| GB | 1-551-832  | * 9/1979 |

* cited by examiner

Primary Examiner—Cecilia J. Tsang
Assistant Examiner—Ebenezer Sackey
(74) Attorney, Agent, or Firm—Oblon, Spivak, McClelland, Maier & Neustadt, P.C.

(57) ABSTRACT

The invention relates to a method for synthesis of aliphatic isocyanates from aromatic isocyanates in substantially 3 stages. In particular, the invention relates to a method for synthesis of bis{4-isocyanatocyclohexyl}methane ($H_{12}$MDI) from bis{4-isocyanatophenyl}methane (MDI). More especially, the invention relates to a method for synthesis of $H_{12}$MDI with a trans-trans isomer content of <30%, preferably of <20%, particularly preferably of 5 to 15%.

44 Claims, No Drawings

METHOD FOR SYNTHESIS OF ALIPHATIC ISOCYANATES FROM AROMATIC ISOCYANATES

BACKGROUND OF THE INVENTION

Field of the Invention

The invention relates to a method for synthesis of aliphatic isocyanates from aromatic isocyanates in substantially 3 stages. In particular, the invention relates to a method for synthesis of bis{4-isocyanatocyclohexyl}methane ($H_{12}$MDI) from bis{4-isocyanatophenyl}methane (MDI). More especially, the invention relates to a method for synthesis of $H_{12}$MDI with a trans-trans isomer content of <30%, preferably of <20%, particularly preferably of 5 to 15%.

Synthetic access to isocyanates is possible in several different ways. As an example, tetramethylxylylene diisocyanate (TMXDI) is a product of the classical isocyanate synthesis (U.S. Pat. No. 4,130,577), which is based on the reaction of an alkyl halide with a metal salt of isocyanuric acid. Good yields are obtained with the method, but the unavoidable production of metal chloride is a problem. In addition, long reaction times must be tolerated. The nitrene rearrangements associated with the names Curtius, Lossen and Hofmann are suitable in particular for the laboratory scale. They are based on carboxylic acids as isocyanate precursors (German Patent 19922996; W. Hentschel, Chem. Ber. 17, 1284 (1884)). The oldest option for large-scale industrial synthesis of isocyanates—still widely used even today—is the phosgene route. The basis of this method is the reaction of amines with phosgene as a highly reactive and potent carbonylation agent. From the mechanistic viewpoint, the resulting isocyanate can be regarded as the product of an addition-elimination sequence. Two fundamental process-engineering alternatives are available: solvent phosgenation (German Patent 19942299, U.S. Pat. No. 4,922,005, European Patents 0175117 and 0716079) and gas-phase phosgenation (U.S. Pat. No. 4,847,408, European Patent 0676392, German Patent 19800529). In the solvent method, the sequence of phosgene addition and HCl elimination proceeds in the solvent, while in the case of gas-phase phosgenation the process takes place in the gas space. The second alternative is a modern technology that offers several advantages, including improved space time yield and the possibility of obtaining special isocyanates with much higher yields (European Patents 0764633 and 0749958). A disadvantage of both phosgenation methods is the use of phosgene, which must be handled according to particularly stringent requirements on the industrial scale because of its toxicity and corrosiveness.

Numerous suggestions have therefore been made on circumventing the use of phosgene for the synthesis of isocyanates on the industrial scale. Phosgene-free process is a term that frequently crops up in connection with the conversion of amines to isocyanates using alternative carbonylation agents such as urea or dialkyl carbonate (European Patents 0018586 and 0355443, U.S. Pat. No. 4,268,683, European Patent 0990644). Further phosgene-free technologies are based on reductive carbonylation of aromatic nitro groups or on oxidative carbonylation of aromatic amino functions as the initial step of a reaction sequence leading to the isocyanate (German Offenlegungsschrifts (Unexamined Application) 2343826 and 2635490; F. J. Weigert, J. Org. Chem. 38 (1973), 1316; S. Fukuoka et al., J. Org. Chem. 49 (1984), 1458).

Heretofore only the urea technology among the phosgene-free processes has been successfully established as a commercially competitive, large-scale industrial alternative to the phosgene process (European Patents 0018586, 0126299, 0126300, 0143320, 0355443, 0566925 and 0568782). The basis of the urea route is the urea-mediated conversion of amines to isocyanates by a two-stage process. In the first step, an amine and an alcohol are converted to a urethane in the presence of urea, and this urethane is then thermally dissociated to isocyanate and alcohol in the second step (European Patents 0355443, 0568782, 0566925 and 0524554).

In another alternative to the synthesis of cycloaliphatic isocyanates, cycloaliphatic urethanes containing one or more urethane groups are first synthesized by catalytic hydrogenation of the corresponding mononuclear or polynuclear aromatic urethanes containing one or more urethane groups and possibly other substituents, and then the cycloaliphatic urethanes are converted to the corresponding cycloaliphatic diisocyanates by elimination of the alcohol groups.

It is also known that, during hydrogenation of the said aromatic urethanes, there are formed aliphatic urethanes in which cis-trans isomerism is possible. In the case of hydrogenation of MDU to $H_{12}$MDU, three cis-trans isomers are possible: cis-trans-, cis-cis- and trans-trans-$H_{12}$MDU. The elimination of the alcohol groups of a mixture of $H_{12}$MDU isomers to form bis{4-isocyanstocyclohexyl}methane leads to a mixture of $H_{12}$MDI isomers whose proportions are substantially equal to the proportions of the $H_{12}$MDU isomers in the starting product.

The practical industrial properties of $H_{12}$MDI are directly related to the proportion of isomers, especially to the content of the 4,4'-trans-trans isomers. In order to ensure constant product quality of the polyurethanes synthesized from the $H_{12}$MDI and to achieve easier handling capability, it is particularly important that the $H_{12}$MDI have the form, at room temperature, of a homogeneous liquid that does not contain solids. The temperature at which the first solid particles form in the $H_{12}$MDI becomes lower with increasing content of the 4,4'-trans-trans isomer. Thus products with low 4,4'-trans-trans content are liquid in a broader temperature range and therefore have considerable advantages for industrial application.

As already mentioned in the foregoing, the proportion of isomers in an $H_{12}$MDI synthesized from $H_{12}$MDU by elimination of the alcohol groups is substantially equal to the proportion of isomers in the $H_{12}$MDU itself. Thus, if a low 4,4'-trans-trans content is to be achieved in the $H_{12}$MDI, it will be particularly economic to produce an $H_{12}$MDU with low 4,4'-trans-trans content during hydrogenation of the MDU, so that it can then be directly further processed to an $H_{12}$MDI with correspondingly low 4,4'-trans-trans content.

As follows from the documents cited hereinafter, the hydrogenation of aromatic urethanes to the corresponding cycloaliphatic urethanes is achieved in some cases by using supported catalysts.

U.S. Pat. No. 5,360,934 teaches the method of the class in question, but uses a supported catalyst containing rhodium for the purpose. Ruthenium can also be present as the active metal. According to the teaching of that document, the catalyst activity depends considerably on the modification of the aluminum oxide used as support. Apparently catalysts containing delta, theta and kappa aluminum oxide are more active as support material than a catalyst containing commercial gamma aluminum oxide as support material.

In the method according to European Patent 0813906, organic compounds can be hydrogenated using a supported ruthenium catalyst. These compounds also include aromatic compounds in which at least one functional group is bonded to an aromatic nucleus. In addition to ruthenium, the catalyst can also contain other metals from the subgroups of Groups I, VII or VIII of the Periodic Table. The support material has a BET surface of at most 30 m²/g and an average pore diameter of at least 50 nm. The catalyst used here is also characterized by a ratio of surface area of the active metal to surface area of the catalyst support of smaller than 0.05. The macroporous support materials with an average pore diameter of preferably 500 nm to approximately 50 µm are mainly aluminum oxide and zirconium oxide. Details on the hydrogenation of MDU to HMDU cannot be inferred from that document. In particular, there is described the hydrogenation of substituted aromatic compounds, in which either at least one hydroxy group or one amino group is bonded to an aromatic nucleus. In contrast, the object set by the inventors of the present application was to convert substituted aromatic urethanes to cycloaliphatic urethanes with low 4,4'-trans-trans content.

A method similar to that of European Patent 0813906 is taught in European Patent 0814098. In this case there are used, as support material for the supported ruthenium hydrogenation catalyst, materials in which 10 to 50% of the pore volume is represented by macropores with a pore diameter ranging from 50 to 10,000 nm and 50 to 90% is represented by mesopores with a pore diameter ranging from 2 to 50 nm. The BET surface of the support is specified as 50 to 500 m²/g, especially 200 to 350 m²/g. The ratio of the surface area of the active metal to that of the support is supposed to be smaller than 0.3, especially smaller than 0.1. Particulars on the activity of such catalysts and on the proportions of isomers during the hydrogenation of MDU to $H_{12}$MDU cannot be inferred from that document.

From European Patent 0653243 there are known catalysts suitable for hydrogenation of aromatic compounds. The catalysts listed therein are systems formed by introduction of the dissolved active component into an organic polymer. This mixture must be mixed in turn with a support material, then molded and heat-treated. This method of producing the catalyst is relatively complex, since numerous individual partial steps must be considered. In total, these steps are cost-intensive, since several chemical additives are necessary. Moreover, the active component becomes homogeneously mixed with the support compound, and so only part of this component is available for catalytic reaction.

German Unexamined Application 2639842 describes a method for synthesis of cycloaliphatic urethanes by hydrogenation of aromatic urethanes. Transition metals of Group Vill of the Periodic Table are used as hydrogenation catalysts, rhodium being particularly preferred. Among other reactions, the hydrogenation of dimethyl 4,4'-methylenedicarbanilate to dimethyl 4,4'-methylenedicyclohexylcarbamate is also described. The hydrogenation reaction is performed in an inert solvent, preferably an aliphatic alcohol. A disadvantage of this method is that the catalysts used rapidly lose activity and can be only partly regenerated by rinsing with sulfuric acid, methanol and 2-propanol. Moreover, no particulars are given regarding the 4,4'-trans-trans content in the product and, moreover, no indication of any kind can be found that this is of importance.

In German Unexamined Application 4407019 there is described a method for synthesis of cycloaliphatic isocyanates from aromatic isocyanates. The method comprises three reaction steps:

1. Reaction of an aromatic urethane with an alcohol (urethanization), preferably methanol. Urethanization takes place "in a manner known in itself" (claim 5).

2. Hydrogenation of the aromatic urethane in an inert solvent with metals of Group VIII of the Periodic Table or compounds thereof as hydrogenation catalysts, ruthenium being particularly preferred.

3. Elimination of the alcohol and liberation of the isocyanate "in a manner known in itself" (claim 5).

The synthesis of $H_{12}$MDI from MDI is cited as an example. This example describes the hydrogenation of dimethyl 4,4'-methylenedicarbanilate to dimethyl 4,4'-methylenedicyclohexylcarbamate. Particulars on the 4,4'-trans-trans content of the product cannot be inferred from the document. Supported catalysts are mentioned only in passing.

From European Patent 0023649 there is known a method for synthesis of aliphatic isocyanates from aromatic cyanates, characterized in that an aromatic isocyanate is first reacted with a lactam and, in a subsequent step, the nucleus of the lactam-blocked isocyanate is hydrogenated with a rhodium catalyst. The lactam is thermally eliminated in order to obtain the free aliphatic isocyanate. A disadvantage is that the lactam-blocked aromatic isocyanates already dissociate back to isocyanate and lactam at relatively low temperatures, thus leading to losses of yield and to deactivation of the catalyst. To ensure low reaction temperatures, there are therefore used exclusively rhodium-based catalysts, which are very expensive because of the fact that the price of rhodium is relatively high compared to that of ruthenium. From the examples presented in European Patent 0023649, it follows that a product with a 4,4'-trans-trans isomer content of 32.1% results during the conversion of MDI to $H_{12}$MDI. According to the description, and as expected, this product is no longer completely liquid at room temperature, but contains crystals.

European Patent 0268856 teaches a method for synthesis of aralkylurethanes, monourethanes and diurethanes by acid-catalyzed addition of formaldehyde and carbamic acid esters to aromatics. The products synthesized in this way can either be dissociated directly to aromatic isocyanates or their nuclei can be hydrogenated first, before they are dissociated to liberate the aliphatic isocyanates. No indications can be found as to the distribution of cis-trans-isomers in the products. In particular, a method for synthesis of $H_{12}$MDU cannot be inferred from the document.

The object of the present invention is to provide a method for synthesis of aliphatic isocyanates from aromatic isocyanates by using a ruthenium-containing supported catalyst, with which the desired cycloaliphatic isocyanates can be obtained with high selectivity. Another object of the invention is to provide a method for synthesis of $H_{12}$MDI, wherein the 4,4'-trans-trans isomer content of the $H_{12}$DMU is smaller than 30%, preferably smaller than 20%, particularly preferably, 5 to 15%. A further object is to ensure that the 4,4'-trans-trans content remains low despite high conversion. According to yet another object, the catalyst used in the method should have a long useful life and the distribution of isomers should remain substantially unchanged even after prolonged operating time.

The subject matter of the invention is a method for synthesis of aliphatic isocyanates from the corresponding aromatic isocyanates, which contain one or more aromatic rings and one or more isocyanate groups bonded directly and/or indirectly to one aromatic ring or to different aromatic rings, comprising substantially the three following stages:

1. urethanization of the aromatic isocyanate, 2. hydrogenation of the aromatic urethane with hydrogen in the presence of a supported catalyst, which contains as active metal, applied on a support, ruthenium alone or together with at least one metal of the subgroups of Groups I, VII or VIII of the Periodic Table, the proportion of active metal being 0.01 to 20 wt % relative to the supported catalyst, and wherein the catalyst support has a BET surface ranging from larger than 30 $m^2/g$ to smaller than 70 $m^2/g$ and more than 50% of the pore volume of the catalyst support is represented by macropores with a pore diameter of larger than 50 nm and less than 50% is represented by mesopores with a pore diameter of 2 to 50 nm, 3. dissociation of the hydrogenated urethane to the aliphatic isocyanate.

The dependent claims relate to preferred embodiments of the inventive method.

As regards the prior art evaluated thoroughly hereinabove, especially European Patent 0814098, it was surprising that a catalyst support with a specific surface ranging from larger than 30 $m^2/g$ to smaller than 70 $m^2/g$ is particularly active in the method of the class in question when more than 50% of the pore volume is represented by macropores and less than 50% of the pore volume is represented by mesopores. Thus it is not the BET surface alone or the pore distribution alone that is important, but instead the combination of these two features. Finally, the catalyst to be used in the method according to the present invention differs in principle from the catalyst cited in European Patent 0813906 by the fact that the catalyst support in the prior art method is indeed macroporous, but the BET surface is at most 30 $m^2/g$ and preferably at most 15 $m^2/g$. The ratio of the surface area of the active metal to that of the catalyst support ranges from 0.01 to 0.5, especially from 0.03 to 0.3. Surprisingly, even a small ratio, on the order of 0.03 to 0.06, of the surface area of the active metal, determined by CO chemisorption, to that of the catalyst support, determined by the BET method, leads to high catalyst activity under mild conditions for the catalyst to be used according to the invention.

It was surprisingly found that isocyanates with low trans-trans-isomer proportions of smaller than 30% are obtained by the inventive method in combination with the catalysts used according to the invention. In particular, the method is also suitable for synthesis of hydrogenation products with trans-trans isomer content of smaller than 20%, especially of 5 to 15%, from bridged binuclear starting products, such as mentioned in the next section.

The method is suitable in particular for synthesis of bis{4-isocyanatocyclohexyl}methane ($H_{12}MDI$) with a trans-trans isomer content of <30%, preferably of <20%, particularly preferably of 5 to 15%.

By means of the inventive method, it is possible to convert aromatic isocyanates of any kind to the corresponding cycloaliphatic isocyanates. These aromatic isocyanates can be mononuclear or polynuclear aromatic compounds. Preferably the aromatic compounds are mononuclear and binuclear aromatic isocyanates or diisocyanates or triisocyanates. The aromatic isocyanates can be substituted on the aromatic nucleus or nuclei or/and on the isocyanate group, for example by one or more alkyl and/or alkoxy groups, preferably $C_{1-20}$ alkyl and/or $C_{1-20}$) alkoxy groups. Particularly preferred substituents are $C_{1-10}$ alkyl groups, especially methyl, ethyl, propyl, isopropyl, butyl, isobutyl and tert-butyl groups; among the alkoxy groups there are preferred the $C_{1-8}$ alkoxy groups, especially methoxy, ethoxy, propoxy and butoxy. The aromatic nucleus or nuclei as well as the alkyl and alkoxy groups can be substituted if necessary by halogen atoms, especially fluorine atoms, or can have other suitable inert substituents or substituents that are amenable to hydrogenation.

The aromatic isocyanate can also have several aromatic nuclei linked by a divalent hydrocarbon group, such as a methylene group or ethylene group, and one or both aromatic nuclei can have a further isocyanate group and/or a $C_1$ to $C_3$ alkyl or alkoxy group. The linking group can have one or more alkyl substituents, especially $C_{1-20}$ alkyl groups, preferably one or more methyl, ethyl, n-propyl, isopropyl, n-butyl, sec-butyl or tert-butyl groups.

Particularly preferred aromatic isocyanates are the compounds listed hereinafter and described by formulas:

bis {4-isocyanatophenyl}methane, 2-isocyanatophenyl-4'-isocyanatophenylmethane, 2-isocyanatophenyl-2'-isocyanatophenylmethane (MDI) and polynuclear methylene-bridged isocyanatophenyls (PMDI) as well as mixtures thereof,

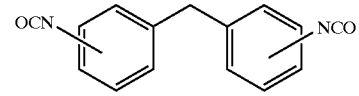

MDI

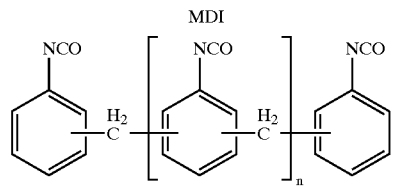

PMDI, n = 1–10

4,4'-dimethyl-3,3'-diisocyanatodiphenylmethane, 2,4'-dimethyl-3,3'-diisocyanatodiphenylmethane, 2,2'-dimethyl-3,3'-diisocyanatodiphenylmethane as well as mixtures thereof,

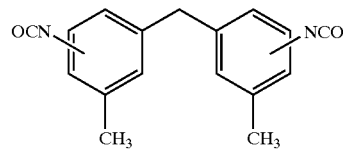

1,2-diisocyanatobenzene, 1,3-diisocyanatobenzene and 1,4-diisocyanatobenzene as well as mixtures thereof,

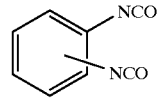

2,4-diisocyanatotoluene and 2,6-diisocyanatotoluene as well as mixtures thereof,

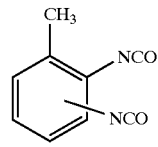

1,6-diisocyanatonaphthalene,

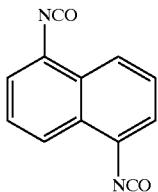

MXDI and TMXDI

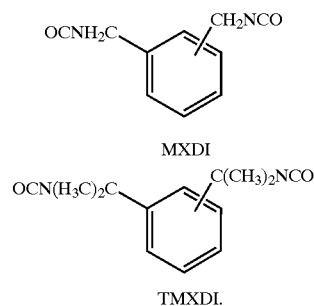

Preferably MDI is used.

Urethanization

The reaction of isocyanates with alcohols is known and has already been described frequently in the technical literature (for example, Ullmann's Encyclopedia of Industrial Chemistry, $4^{th}$ Edition, Volume 19, pages 310 to 340).

The reaction can take place in pure substance, although solvents are usually used to lower the viscosity. All liquids known to be inert to the reaction partners can be chosen as solvents. Examples therefore include ketones such as acetone and methyl ethyl ketone, aromatics such as toluene and xylenes, amides such as dimethylformamide and N-methylpyrrolidone, ethers such as diethyl ether, dioxane and tetra hydrofuran, and esters such as ethyl acetate, butyl acetate and methoxypropyl acetate. Obviously mixtures of solvents are also possible.

The solvents in question should be anhydrous if at all possible (water content <0.1 wt %).

All primary, secondary or tertiary monohydric alcohols can be used as alcohols, including methanol, ethanol, propanol, isopropanol, n-butanol, 2-butanol, sec-butanol, tert-butanol, n-pentanol, 2-pentanol, 3-pentanol, isopentanol, neopentyl alcohol, hexanol, cyclohexanol and ethylhexanol. Obviously mixtures of alcohols are also possible.

The ratio of isocyanate groups to alcohol groups is adjusted such that at least one alcohol group is present for each isocyanate group. In the usual case, however, an excess of alcohols will be used. The excess can be as high as 100 times the isocyanate equivalent. In this case the alcohol component functions additionally as a solvent.

The reaction of isocyanates, especially MDI, with alcohols, especially n-butanol, is usually performed at temperatures of 20 to 160° C., preferably at 40 to 120° C., and normal pressure.

The reaction time—usually between 20 minutes and 10 hours—can be influenced by means of parameters such as temperature, monomer concentration and monomer reactivity.

Moreover, the reaction can also be accelerated with catalysts, as has already long been known in urethane chemistry. Possibilities include metal-containing catalysts, such as dibutyltin dilaurate and zinc octoate, and tertiary amines such as triethylamine and 1,4-d diazabicyclo-(2,2,2)-octane.

Vessels equipped with stirrers or cascades of such vessels, in continuous or batchwise operation, can be used as reaction vessels, as can flow tubes or extruders. The latter machines are suitable in particular for the case in which solvent is not used. The choice of a suitable extruder is a familiar task to those skilled in the art (see "Screw-Type Machines in Process Engineering", H. Hermann, Springer Verlag, Berlin, Heidelberg, N.Y., 1972).

Hydrogenation

The aromatic urethanes that are particularly preferred for hydrogenation are the compounds listed hereinafter and described by formulas:

dialkyl 4,4'-methylenedicarbanilate, dialkyl 2,4'-methylenedicarbanilate, dialkyl 2,2'-methylenedicarbanilate and polynuclear methylene-bridged alkyl carbanilates (PMDU) as well as mixtures thereof,

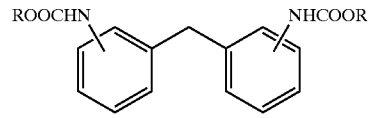

$R=C_1-C_6$ alkyl, preferably n-butyl

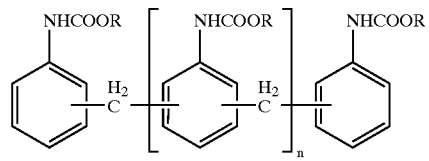

PMDU, $R=C_1-C_6$ alkyl, preferably n-butyl, n=1 to 10 dialkyl 4,4'-methylene-3,3'-dicarbanilate, dialkyl 2,4'-methylene-3,3'-dicarbanilate, dialkyl 2,2'-methylene-3,3'-dicarbanilate as well as mixtures thereof,

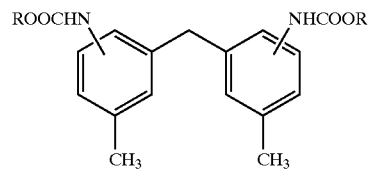

$R=C_1-C_8$ alkyl, preferably n-butyl dialkyl 1,2-phenyldicarbamate, dialkyl 1,3-phenyldicarbamate and dialkyl 1,4-phenyldicarbamate as well as mixtures thereof,

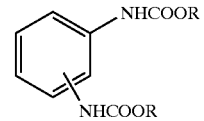

$R=C_1-C_6$ alkyl, preferably n-butyl dialkyl 2,4-toluenedicarbamate, dialkyl 2,6-toluenedicarbamate as well as mixtures thereof

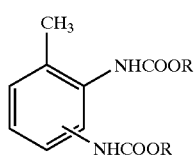

R=C$_1$–C$_6$ alkyl, preferably n-butyl
dialkyl 1,6-naphthalenedicarbamate,

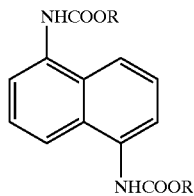

R=C$_1$–C$_6$ alkyl, preferably n-butyl
the urethanes corresponding to the compounds abbreviated as MXDI and TMXDI,

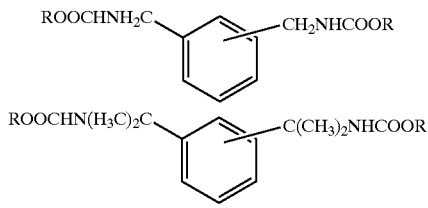

(R=alkyl, preferably n-butyl)

Preferred compounds are dialkyl 4,4'-(C$_1$ to C$_4$)alkanedicarbanilate and/or a 2,4'-isomer and/or 2,2'-isomer or mixtures thereof, particularly preferably dibutyl 4,4'-methylenedicarbanilate or an isomer or a mixture (MDU). In particular, dibutyl 4,4'-methylenedicarbanilate is hydrogenated to dibutyl 4,4'-methylenedicyclohexylcarbamate with a trans-trans isomer content of <30%, preferably of <20%, particularly preferably of 5 to 15%.

The supported catalysts to be used according to the invention can be synthesized industrially by application of ruthenium and if necessary of at least one metal of the subgroups of Groups I, VII or VIII on a suitable support. Application can be achieved by immersion of the support in aqueous solutions of metal salt, such as solutions of ruthenium salt, by spraying appropriate solutions of metal salt onto the support or by other suitable methods. Suitable salts for preparation of the solutions of ruthenium salts as well as solutions of metal salts of elements of the subgroups of Groups I, VII or VIII include the nitrates, nitrosylnitrates, halides, carbonates, carboxylates, acetylacetonates, chlorine complexes, nitro complexes or amine complexes of the corresponding metals; nitrates and nitrosylnitrates are preferred.

In catalysts that contain further metals applied on the support in addition to ruthenium, the metal salts or solutions of metal salts can be applied simultaneously or consecutively.

The supports coated or impregnated with a ruthenium salt or additionally with further solutions of metal salts are dried, preferably at temperatures of between 100 and 150° C., and optionally are calcined at temperatures of between 200 and 600° C. Thereafter the coated supports are activated by treating the coated supports in a gas stream containing free hydrogen at temperatures of between 30 and 600° C., preferably of between 150 and 400° C. The gas stream is preferably composed of 50 to 100 vol % of H$_2$ and 0 to 50 vol % of N$_2$.

If one or more other metals of the subgroups of Groups I, VII or VIII is applied onto the supports in addition to ruthenium, and if such application takes place consecutively, the support can be dried at temperatures of between 100 and 150° C. after each application or impregnation and optionally calcined at temperatures of between 200 and 600° C. The sequence in which the solutions of metal salts is applied can be chosen as desired.

According to a preferred embodiment, the support is coated by spraying it with a solution of metal salt at elevated temperature, especially above 50° C. and particularly preferably at 80 to 150° C., so that the solvent is already evaporated at least partly during the coating operation and the depth of penetration of the catalytically effective metals is limited. Preferably the depth of penetration ranges from 5 to 250 μm, especially from 10 to 150 μm and particularly preferably from 50 to 120 μm.

The solution of ruthenium salt and if necessary solutions of further metal salts are applied in such a quantity on the support or supports that the proportion of ruthenium and if necessary of other metals of the subgroups of Groups I, VII or VIII applied on the support corresponds to 0.01 to 20 wt % relative to the total weight of the catalyst. Preferably the quantity of active metals corresponds to 0.2 to 15 wt %, especially to about 0.2 to 3 wt %, the ruthenium content exceeding the content of the other metals by an appropriate value.

The support materials of the catalysts to be used according to the invention have a specific BET surface (determined according to DIN 66131, using N$_2$) ranging from larger than 30 m$^2$/g to smaller than 70 m$^2$/g.

The support contains macropores with a pore diameter of larger than 50 nm. The diameter of the macropores ranges in particular from 50 to 50,000 nm, but frequently falls within the range of 50 to 10,000 nm. If the support also contains mesopores, pores in the size range from 2 to 50 nm are to be understood thereby. At least 50% of the pore volume is represented by macropores and less than 50% by mesopores. Preferred supports contain macropores in a proportion of 55 to 85% of the pore volume, and 15 to 45% of the pore volume corresponds to mesopores. In particularly preferred supports, mesopores account for about 25 to 45% of the pore volume and macropores for the rest of the pore volume. Micropores with a pore diameter of smaller than 2 nm, if present at all, represent only a proportion of less than 10% of the pore volume, especially of less than 1%.

The support can comprise uniform or mixed modifications, and so the pore distribution can be monomodal, bimodal or trimodal.

In principle, all known support materials for hydrogenation catalysts can be used, provided they have the BET surface, pore size and pore distribution according to the claims. Suitable supports can be oxides, silicates and nitrides, with single-phase or multiphase crystalline structure, with radiographically amorphous structure or with mixed structure.

The supports can be further modified in known manner by means of alkali metal and or alkaline earth compounds and/or with metals of the lanthanide series.

Examples of supports include oxides from the series comprising Al$_2$O$_3$, TiO$_2$, ZrO$_2$, SiO$_2$, MgO and ZnO, as well as mixed oxides, including spinels such as MgAl$_2$O$_4$. Aluminosilicates and active charcoal are also suitable, provided such supports have the combination of properties according to the claims. Particularly preferred oxides are $Al_2O_3$ and $TiO_2$.

The hydrogenation step is carried out at a temperature ranging from 20 to 250° C., especially below 200° C., and an effective $H_2$ partial pressure ranging from about 1 to 30 MPa, preferably lower than 15 MPa, in a suspension or fixed-bed hydrogenation reactor in continuous or batchwise operation. The activity of the inventive catalysts ensures that the hydrogenation step can be carried out under mild conditions, especially at a temperature ranging from 50 to 150° C., especially 70 to 120° C. and an $H_2$ pressure ranging from 3 to 15 MPa, thus allowing the use of industrially less complex reactors and improving the economy of the method.

A further economic advantage resulting from the mild hydrogenation conditions is an increased total yield of the method. This is due mainly to the fact that dissociation of the urethane back to isocyanate and alcohol becomes more pronounced with rising temperature. Subsequent hydrogenation of the unprotected isocyanate group leads to formation of undesired secondary products, which must be separated from the product and thus cause a loss of yield.

The hydrogenation step can be performed in the presence or absence of a suitable solvent. Preferably a solvent is present, specifically in a proportion of about 10 to 90 wt % relative to the solution of the aromatic urethane to be hydrogenated.

Examples of suitable solvents include primary, secondary and tertiary monohydric or polyhydric alcohols, such as methanol, ethanol, n-propanol, i-propanol, n-butanol, sec-butanol, tert-butanol, ethylene glycol, ethylene glycol mono ($C_1$ to $C_4$)alkyl ether; straight-chain ethers such as ethylene glycol di($C_1$ to $C_3$)alkyl ethers, cyclic ethers such as tetrahydrofuran and dioxane, alkanes such as n-alkanes and iso-alkanes with 4 to 12 C atoms, such as n-pentane, n-hexane and isooctane, and cyclic alkanes such as cyclohexane and decalin.

The hydrogenation product itself, or in other words a cycloaliphatic urethane, can also be a solvent.

In a preferred embodiment of the method, there is used a mixture of two or more solvents, composed of alcohols and ethers, in which the alcohol corresponds in particular to the alcohol group contained in the urethane, preferably n-butanol. The preferred ether is THF. It has been surprisingly found that not only does the alcohol addition lead to an increase of hydrogenation selectivity, which on the basis of the law of mass action is due to the expected decrease of dissociation of the urethane back to alcohol and isocyanate, but also the activity of the catalyst and thus the space-time yield of the overall process are considerably increased. The alcohol content of the solvent mixture varies from 0.1 to 99.9 wt %, preferably lower than 50%, particularly preferably from 5 to 30 wt %.

A fixed-bed reactor is preferred for continuous hydrogenation. The fixed-bed reactor can be operated as a bubble reactor, although a trickling-bed procedure is preferred. A trickling-bed reactor preferably has an LHSV value ranging from 0.1 to 5 $h^{-1}$ (=liters of reaction solution per liter of fixed-bed catalyst per hour). According to a particularly preferred embodiment of the inventive method, there is used a tube reactor operated by the trickling-bed procedure.

Dissociation

In common with the urea method, the majority of all described versions of phosgene-free isocyanate syntheses lead in the next-to-last stage to compounds belonging to the urethane family. Urethanes, which are also known as carbamates, can be regarded as direct isocyanate precursors. The critical step in each case is liberation of the desired isocyanate, especially by thermal dissociation of the parent urethane or carbamate.

In analogous manner, the inventive method also depends in the last step on thermally induced dissociation of urethanes. This can be achieved by means of basically known methods of urethane dissociation, or in other words in the gas or liquid phase, with or without solvent and with or without catalyst (European Patents 0126299, 0126300, 0355443, 0092738, 0396977 and 0396976). As regards urethane dissociation, the inventive method is preferably guided substantially by knowledge from the urea technology according to European Patent 0568782. Process parameters (pressure, temperature, catalyst quantity) that differ in detail from the template result from the fact that the urethanes of the inventive method and of the urea technology have a different history of formation and, although they cannot be basically distinguished from one another for this reason, they do differ as regards the spectrum of secondary products.

By analogy with the cited prior art of urea technology, the unblocking reaction during the inventive method is preferably achieved by thermal dissociation of the urethane in the liquid phase, without using solvents, in the presence of 1 to 2000, preferably 2 to 1000, particularly preferably 5 to 500 ppm of a suitable catalyst, in a combined cracking (dissociation) and rectification column having a bottom temperature of 200 to 300° C., preferably of 215 to 245° C., and a bottom pressure of 1 to 50 mbar, preferably of 5 to 30 mbar. Thereafter the formed isocyanate is drawn off as raw isocyanate via the side outlet of the rectification column, while the alcohol is removed overhead. The combined cracking and rectification column, containing a lower section for dissociation and an upper section for rectification of the dissociated products, should be provided with high-efficiency, preferably ordered packings, and at the bottom should be equipped with a falling-film evaporator for the energy supply thereto. In order to remove the secondary products formed by dissociation, reaction mixture is continuously removed from the bottom in a proportion of 2 to 50 wt %, preferably of 5 to 25 wt % relative to the feed. The urethane to be dissociated is supplied to the bottom third of the column, but alternatively it can also be routed into the circulation to the falling-film evaporator.

By virtue of the reactivity of the isocyanate group and the associated tendency to form undesired higher molecular weight secondary components, it is recommended that the average dwell time in the cracking (dissociation) zone be kept as short as possible. This can be achieved by minimizing the liquid volume by appropriate structural measures and by using ordered packings with small "hold-up" as well as by removing the formed isocyanate from the cracking zone as smoothly as possible by distillation.

Even if the best possible conditions with regard to average dwell time and smooth removal of the formed isocyanate are maintained, the formation of high molecular weight secondary product cannot be completely suppressed. For this reason, a proportion of reaction mixture is continuously drawn from the bottom in order to remove such products. This removal technique largely suppresses resinifcation of the material, and so significant disturbances in the progress of the industrial process, caused by incrustation and fouling of the apparatus, can be prevented.

The raw diisocyanate drawn off from the combined cracking and rectification column is purified by vacuum distillation. In this step, first runnings and distillation residues can be recycled to the combined cracking and rectification column.

Suitable catalysts within the meaning of the inventive method are halides or oxides of metals of Groups IB, IIB, IIIB, IVB, VB, VIB, VIIB and VIIIB of the Periodic Table. Preferably there are used chlorides of zinc or tin as well as oxides of zinc, manganese, iron or cobalt.

Upstream from urethane dissociation there is disposed a rough pre-purification stage, in which the solvents, such as tetrahydrofuran (THF) and excess butanol, are first separated by nitrogen stripping and then the concentrations of further low-boiling secondary components, which were formed in the course of the urethanization/hydrogenation sequence and/or were already present as impurities in the feedstocks, are reduced by means of a two-stage combination of short-path evaporation and thin-film evaporation. If appropriate, the stripping of solvents (such as THF and butanol) upstream from the evaporator combination can also be dispensed with entirely.

Before the purified urethane is fed to the cracking stage, there is added thereto, as an approximately 5% solution or suspension in alcohol, the cracking catalyst, which is also used for synthesis of the urethane, in a proportion of 1 to 2000, preferably of 2 to 1000, particularly preferably of 5 to 500 ppm relative to the volume of the mixture in the cracking reactor.

The invention will be explained in more detail by the following examples.

EXAMPLES

I. Urethanization

Example 157 g (0.63 mol) of MDI was dissolved in 2.2 I of anhydrous tetrahydrofuran (THF) and mixed portion-by-portion with 343 g (4.63 mol) of n-butanol. The solution was heated under reflux (70° C.) for 5 hours with stirring and then cooled. After the solvent (THF and excess butanol) had been drawn off by means of the rotary evaporator, 388 g (99%) of MDU was obtained as a white powder, with a melting point of 115 to 117° C. and an NCO content of 0.8%.

II. Hydrogenation

A. Preparation of the Catalyst:

Example 1

Aluminum oxide molded bodies (extrudate, d=3 mm) with a BET surface of about 33 $m^2/g$ and a bimodal pore distribution with a pore volume of 0.41 ml/g, wherein substantially no pores with a diameter of 2 to 50 nm were observed but 100% of the pore volume was represented by macropores with a diameter in the range of 50 to 10,000 nm, were coated with an aqueous ruthenium(III) nitrate solution at about 90 to 100° C., by spraying the catalyst solution onto the support material while it was being kept in motion, water being evaporated simultaneously. The catalyst solution had a concentration of 5% of metal relative to the weight of the solution. The support coated in this way was heated at a temperature of 120 to 180° C. and then reduced for 4 hours at 200° C. using a mixture of 50% H2 and 50% N2. The catalyst prepared in this way had a content of 3 wt % of ruthenium relative to the total weight of the catalyst. The depth of penetration of the ruthenium was 70 to 90 tcm. The ratio of the ruthenium surface area, determined by CO chemisorption, to the surface area of the uncoated support material, determined by the BET method, was about 0.05. The aluminum oxide molded bodies were composed substantially of alpha and gamma $Al_2O_3$ (about 18 wt % of $SiO_2$ and about 2 wt % of alkali metal and alkaline earth oxides, $Fe_2O_3$ and $TiO_2$).

Example 2

Aluminum oxide molded bodies (extrudate, d=3 mm) with composition similar to that of the support of Example 1 and with a BET surface of about 32 $m^2/g$, trimodal pore distribution and a pore volume of 0.58 ml/g, were impregnated in a manner analogous to that of Example 1. Of the pore volume of the support material, 31% resulted from pores with a diameter of 2 to 50 nm, 44% from pores with a diameter of 50 to 10,000 nm and 25% from pores with a diameter of larger than 10,000 nm up to 5 Pm. The catalyst prepared in this way had a ruthenium content of 3 wt %, as in Example 1, and the depth of penetration was 70 to 90 pm.

Example 3

Aluminum oxide molded bodies (extrudate, d=3 mm) with a surface of about 54 $m^2 1$ g exhibited a trimodal pore distribution and had a pore volume of 0.77 ml/g. Of the pore volume, 40% resulted from pores with a diameter of 2 to 50 nm and 60% from pores with a diameter of 50 to 10,000 nm. Impregnation of the support as well as calcination and reduction of the catalyst were performed in the same way as in Example 1. The catalyst prepared in this way contained 3 wt % of ruthenium relative to the total weight of the catalyst. The depth of penetration was 70 to 90 nm. The aluminum oxide molded bodies used contained the alpha, theta and gamma modifications of $Al_2O_3$.

Example 4

Aluminum oxide molded bodies in the form of spherical pellets having a size of 2 to 4 mm with a BET surface of about 35 $m^2/g$ exhibited, in a monomodal pore distribution, a pore volume of 0.5 ml/g. Of the pore volume, 42% was represented by mesopores (2 to 50 nm) and 58% was represented by macropores (50 to 10,000 nm). The support material contained the theta and gamma $Al_2O_3$ modifications. Impregnation, calcination and reduction were performed in the same way as in Example 1. The supported ruthenium catalyst prepared in this way contained 3 wt % of ruthenium relative to the total weight of the catalyst. The depth of penetration of the ruthenium was 80 to 120 $\mu$m.

Comparison Example 1

Titanium dioxide molded bodies (extrudate, d=2 mm) comprising substantially a mixture of rutile and anatase with a BET surface of 45 $m^2/g$ exhibited, in a monomodal pore distribution, a pore volume of 0.35 ml/g. 100% of the pore volume was represented by mesopores (2 to 50 nm). The molded bodies were impregnated in the same way as in Example 1, but drying was performed at 150 to 160° C. and the subsequent reduction took place at 180° C. for 4 hours. The catalyst prepared in this way contained 3 wt % of ruthenium relative to the total weight of the catalyst. The depth of penetration was 90 to 120 gm.

Comparison Example 2

Aluminum oxide molded bodies (extrudate, d=1.2 nm) comprising substantially gamma $Al_2O_3$ with a BET surface of 220 $m^2/g$ had a pore volume of 0.65 mlig, 95% of the pore volume being represented by mesopores (2 to 50 nm) and 5% of the pore volume being represented by macropores (50 to 10,000 nm. The support was impregnated with an aqueous ruthenium(III) nitrate solution at room temperature. The catalyst solution had a concentration of 5% of metal relative to the weight of the solution. The impregnated support was heated at a temperature of 150 to 160° C. and then reduced for 4 hours at 180° C. using a mixture of 50% H2 and 50% N2. The catalyst prepared in this way had a content of 5 wt % of ruthenium relative to the total weight of the catalyst. The depth of penetration was as much as 600 µm.

B. Performance of the Hydrogenation Reaction

Example 1

Preparation of an MDU solution containing 10 wt % of MDU, 10 wt % of n-butanol and 80 wt % of THF 2400 g of THF (33.3 mol) and 300 g of n-BuOH (4.05 mol) were placed in a 5-liter three-necked flask with stirring apparatus and heatable dropping funnel. The solution was heated to boiling (about 70° C.) and then 188.4 g of MIDI (0.75 mol) was smoothly added dropwise in molten form. The mixture was maintained under reflux until completion of the reaction (about 6 hours). The completeness of the reaction was checked by determination of the NCO number and by IR spectroscopy.

When a different MDU and/or n-butane content was desired, the quantities of starting materials were adapted accordingly.

Example 2

Hydrogenation of MDU solutions with different n-butanol contents in the autoclave at 100° C.

This example is intended to illustrate the influence of n-butanol on the catalyst activity.

By analogy with Example 1, three 10 wt % MDU solutions were prepared with different n-butanol contents (0, 10 and 20 wt % in the final solution, MDI from the Aldrich Co.). These solutions were hydrogenated at 100° C. and 80 bar in a 1-liter laboratory autoclave containing a catalyst basket. In each case there were used 600 g of MDU solution and 48.3 g of inventive catalyst. After 5 hours a sample was removed from the reactor and analyzed by means of HPLC/CLND, HPLC/MS and GC-PTV-MS. The result is presented in Table 1. It can be clearly seen that, with increasing n-butanol content in the reaction mixture, fewer hydrogenable intermediate products are present in the end product after 5 hours, while the $H_{12}$MDU content is higher. This is equivalent to a distinct increase of the rate of reaction. According to the invention the content of the 4,4'-trans-trans isomer is low, with a value of about 8%.

TABLE 1

Result of hydrogenation of MDU solution with different n-butanol contents.
Hydrogenation conditions: 100° C., 80 bar. All values in wt %.

| Reaction mixture No. Starting mixture composition | 1 | 2 | 3 |
| --- | --- | --- | --- |
| MDU | 10 | 10 | 10 |
| THF | 90 | 80 | 70 |
| n-Butanol | 0 | 10 | 20 |
| Product composition[1] | | | |
| MDU | 6.8 | 0 | 0 |
| Hydrogenable Intermediate products[2] | 54.9 | 15 | 3.3 |
| $H_{12}$MDU | 36.4 | 81.9 | 92.3 |
| Secondary products | 1.9 | 3.1 | 4.4 |
| 4,4'-Trans-trans content[3] | 7 | 8 | 8 |

[1]After subtraction of n-butanol and THF.

TABLE 1-continued

Result of hydrogenation of MDU solution with different n-butanol contents.
Hydrogenation conditions: 100° C., 80 bar. All values in wt %.

[2]Only those that can be further hydrogenation to $H_{12}$MDU in the further course of the reaction.
[3]Proportion of trans-trans-$H_{12}$MDU relative to the sum of the contents of all $H_{12}$MDU isomers.

Example 3

Hydrogenation of MDU solutions with different n-butanol contents in the autoclave at 120° C.

This example is intended to illustrate the positive influence of n-butanol on the selectivity.

By analogy with Example 1, three 10 wt % MDU solutions were prepared with different n-butanol contents (0, 10 and 20 wt % in the final solution, MDI from the Aldrich Co.). These solutions were hydrogenated at 120° C. and 80 bar in a 1-liter laboratory autoclave containing a catalyst basket. In each case there were used 600 g of MDU solution and 48.3 g of inventive catalyst. After 4 hours a sample was removed from the reactor and analyzed by means of HPLC/CLND, HPLC/MS and GC-PTV-MS. The result is presented in Table 2. In all experiments, hydrogenable intermediate product is no longer detectable after 4 hours. It can be clearly seen that, with increasing n-butanol content in the reaction mixture, the proportion of secondary product decreases. This is equivalent to a distinct increase of the selectivity. According to the invention the content of the 4,4'-trans-trans isomer is low, with a value of about 8%.

TABLE 2

Result of hydrogenation of MDU solution with different n-butanol contents.
Hydrogenation conditions: 120° C., 80 bar. All values in wt %.

| Reaction mixture No. Starting mixture composition | 1 | 2 | 3 |
| --- | --- | --- | --- |
| MDU | 10 | 10 | 10 |
| THF | 90 | 80 | 70 |
| n-Butanol | 0 | 10 | 20 |
| Product composition[1] | | | |
| MDU | 0 | 0 | 0 |
| Hydrogenable Intermediate products[2] | 0 | 0 | 0 |
| $H_{12}$MDU | 92 | 93.5 | 94.8 |
| Secondary products | 8 | 6.5 | 5.2 |
| 4,4'-Trans-trans content[3] | 8 | 7 | 7 |

[1]After subtraction of n-butanol and THF.
[2]Only those that can be further hydrogenation to $H_{12}$MDU in the further course of the reaction.
[3]Proportion of trans-trans-$H_{12}$MDU relative to the sum of the contents of all $H_{12}$MDU isomers.

Example 4

Hydrogenation of MDU Solutions with Different n-butanol Contents in the Trickling-bed Reactor at 100° C.

By analogy with Example 1, three 10 wt % MDU solutions were prepared with different n-butanol contents (0, 5 and 10 wt % in the final solution). These solutions were hydrogenated at 100° C. and 80 bar in a trickling-bed reactor packed with 14.5 g of inventive catalyst. The removed samples were analyzed by means of HPLC/CLND, HPLC/MS and GC-PTV-MS. The result is presented in Table 3.

It can be clearly seen that, with increasing n-butanol content in the reaction mixture, the proportion of secondary product decreases. This is equivalent to a distinct increase of the selectivity. At the same time the proportion of unreacted MDU decreased. According to the invention the content of the 4,4'-trans-trans isomer is low, with a value of about 8.9 to 9.8%.

TABLE 3

Result of continuous hydrogenation of MDU solution with different n-butanol contents.
Hydrogenation conditions: 100° C., 80 bar. All values in wt %.

| Reaction mixture No. | 1 | 2 | 3 |
|---|---|---|---|
| Starting mixture composition | | | |
| MDU | 10 | 15 | 10 |
| THF | 90 | 80 | 80 |
| n-Butanol | 0 | 5 | 10 |
| Product composition[1)] | | | |
| MDU | 8.6 | 0 | 0 |
| Hydrogenable Intermediate products[2)] | 47.6 | 0.4 | 0 |
| $H_{12}$MDU | 39.1 | 95.7 | 98.1 |
| Secondary products | 4.6 | 3.9 | 2.0 |
| 4,4'-Trans-trans content[3)] | 9.6 | 8.9 | 9.8 |

[1)]After subtraction of n-butanol and THF.
[2)]Only those that can be further hydrogenation to $H_{12}$MDU in the further course of the reaction 46680046.
[3)]Proportion of trans-trans-$H_{12}$MDU relative to the sum of the contents of all $H_{12}$MDU isomers.

III. Dissociation
A. Working-Up of an $H_{12}$MDU-Containing THF-butanol Solution from Hydrogenation The THF-butanol solution obtained from hydrogenation contained about 20% of $H_{12}$MDU and a solvent proportion of about 80%, depending on the efficiency of the upstream flash stage.

To prevent peroxide formation during working up, this solution was continuously worked up in a two-stage short-path/thin-film evaporator system. For safety reasons, it was recommended that short contact times between product and heating surface be maintained.

Example 2500 g/h of the $H_{12}$MDU-containing THF-butanol solution was treated continuously in a short-path evaporator operated at 140° C. and 700 mbar. The resulting distillate was condensed at −5° C. Over a period of 7 hours, there was obtained 13,903 g of distillate. The distillate was free of $H_{12}$MDU and its composition corresponded to 81% THF and 19% butanol.

The outlet stream of the short-path evaporator was passed to a thin-film evaporator with top-mounted column, in order to separate the remaining THF-butanol mixture as well as low-boiling impurities. The purpose of the top-mounted column was to hold up entrained $H_{12}$MDU.

Distillation in the thin-film evaporator took place at 230° C. and 8 mbar. Meanwhile the top-mounted column was kept heated at 170° C. The overhead product was also condensed at −5° C. Within the described period there were obtained 246 g of overhead product and 3,220 g of $H_{12}$MDU. Butanol-THF represented 70% of the composition of the overhead product and components of the first runnings accounted for the other 30%.

The $H_{12}$MDU contained <0.05% of THF and <0.5% of butanol. It was suitable for direct feed to dissociation, without further purification by distillation.

B. Thermal Dissociation of $H_{12}$MDU to $H_{12}$MDI and Butanol

Dissociation took place in a combined cracking and rectification column at 230° C. and 10 mbar, in the presence of about 10 to 20 ppm of tin(II) chloride as catalyst.

The formed diisocyanate was collected as raw diisocyanate from the side outlet, while the pure alcohol was drawn off overhead. The combined cracking and rectification column was equipped with a failing-film evaporator for the energy supply. The $H_{12}$MDU and the catalyst were injected into the circulation of the falling-film evaporator.

Example

Molten $H_{12}$MDU (140° C.) was injected at a rate of 750 g per hour into the circulation of the falling-film evaporator of the cracking and rectification column. The gaseous $H_{12}$MDI and butanol obtained from dissociation were condensed out at 85° C. and −25° C. in two condensers connected in series. The raw $H_{12}$MDI obtained, with a purity of about 97%, was subjected to pure distillation, which yielded 400 g/h of $H_{12}$MDI with a purity of >99.5%. 260 g/h of butanol was collected as overhead product of the cracking and rectification column. This butanol had a purity of >99.5% and contained trace amounts of monoisocyanato-monourethane as impurity. To maintain constant mass inside the cracking and rectification column and to prevent incrustation and fouling of the cracking apparatus, 60 g/h was drawn off from the circulation.

The disclosure of the priority document, German Patent Application No. 10253803.4, filed Nov. 18, 2002, is incorporated by reference herein in its entirety.

What is claimed is:

1. A method for synthesizing an aliphatic isocyanate from an aromatic isocyanate which has one or more aromatic rings and one or more isocyanate groups bonded directly, indirectly or both directly and indirectly to one or more of the aromatic rings, the method comprising:
   i. urethanizing the aromatic isocyanate to form an aromatic urethane, wherein the urethanizing is carried out continuously or batchwise, in the presence or absence of a solvent or solvent mixture, and in the presence or absence of a catalyst, at temperatures of 20° C. to 160° C., and under normal pressure;
   ii. hydrogenating the aromatic urethane with hydrogen in the presence of a supported catalyst to form a hydrogenated urethane, where the supported catalyst comprises as an active metal, applied on a catalyst support, ruthenium, alone or together, with at least one metal of Group I, VII or VIII of the Periodic Table, wherein the proportion of the active metal is 0.01 to 20 wt % relative to the weight of the supported catalyst, and wherein the catalyst support has a BET surface area from greater than 30 m$^2$/g to less than 70 m$^2$/g, and more than 50% of the pore volume of the catalyst support is comprised of macropores with a pore diameter of larger than 50 nm, and less than 50% of the pore volume of the catalyst support is comprised of mesopores with a pore diameter of 2 to 50 nm; and
   iii. dissociating the hydrogenated urethane to the aliphatic isocyanate.

2. The method according to claim 1, wherein the aromatic isocyanate is at least one selected from the group consisting of bis{4-isocyanatophenyl}methane, 2-isocyanatophenyl-4'-isocyanatophenylmethane, 2-isocyanatophenyl-2'-isocyanatophenylmethane (MDI), a polynuclear methylene-bridged isocyanatophenyl (PMDI), 4,4'-dimethyl-3,3'- diisocyanatodiphenylmethane, 2,4'-dimethyl-3,3'-diisocyanatodiphenylmethane, 2,2'-dimethyl-3,3'-diisocyanatodiphenylmethane, 1,2-diisocyanatobenzene, 1,3-diisocyanatobenzene, 1,4-disocyanatobenzene, 2,4-diisocyanatotoluene, 2,6-diisocyanatotoluene, 1,6-diisocyanatonaphthalene, xylylene diisocyanate (MXDI) and tetramethylxylylene diisocyanate (TMXDI).

3. The method according to claim 1, wherein the urethanizing step is carried out in an alcohol.

4. The method according to claim 1, wherein the urethanizing step is carried out in n-butanol.

5. The method according to claim 1, wherein the active metal applied on the catalyst support has a depth of penetration into the catalyst support of from 20 to 500 $\mu$m.

6. The method according to claim 1, wherein the active metal applied on the catalyst support has a depth of penetration into the catalyst support of from 25 to 250 $\mu$m.

7. The method according to claim 1, wherein a ratio of the surface area of the active metal, determined by CO pulse chemisorption, to the surface area of the catalyst support, determined by the BET method, is greater than 0.01.

8. The method according to claim 1, wherein a ratio of the surface area of the active metal, determined by CO pulse chemisorption, to the surface area of the catalyst support, determined by the BET method, is from 0.03 to 0.3.

9. The method according to claim 1, wherein the catalyst support is at least one selected from the group consisting of a crystalline oxide, an amorphous oxide, a crystalline silicate and an amorphous silicate.

10. The method according to claim 1, wherein the catalyst support is at least one selected from the group consisting of $Al_2O_3$, $SiO_2$, $TiO_2$, $ZrO_2$, MgO, ZnO and an aluminosilicate.

11. The method according to claim 1, wherein the catalyst support has a BET surface area of from 32 to 67 $m^2/g$, the depth of penetration of the active metal ranges from 50 to 200 $\mu$m and the Ru content is from 0.2 to 3 wt % relative to the catalyst, and at least 55% of the pore volume of the catalyst support is comprised of macropores and less than 45% is comprised of mesopores.

12. The method according to claim 1, wherein the hydrogenating step is carried out in a suspension or fixed-bed hydrogenation reactor, continuously or batchwise, at a temperature of from 20 to 250° C., and a hydrogen partial pressure of from 1 to 30 MPa.

13. The method according to claim 1, wherein the hydrogenating step is carried out in a fixed-bed reactor.

14. The method according to claim 1, wherein the hydrogenating step is carried out in a tube reactor by a trickling-bed procedure.

15. The method according to claim 1, wherein the supported catalyst was produced by applying the active metal ruthenium onto the catalyst support by spraying the catalyst support with a ruthenium solution at a temperature of at least 80° C., with subsequent heat treatment and activation of the catalyst by reduction in a hydrogen-containing gas.

16. The method according to claim 1, wherein the supported catalyst was produced by applying the active metal ruthenium onto the catalyst support by spraying the catalyst support with a ruthenium nitrosylnitrate solution at a temperature of at least 80° C., with subsequent heat treatment and activation of the catalyst by reduction in a hydrogen-containing gas.

17. The method according to claim 1, wherein the aromatic urethane is at least one selected from the group consisting of a $C_1$–$C_6$ dialkyl 4,4'-methylenedicarbanilate, a $C_1$–$C_6$ dialkyl 2,4'-methylenedicarbanilate, a $C_1$–$C_6$ dialkyl 2,2'-methylenedicarbanilate, a $C_1$–C6 polynuclear methylene-bridged alkyl carbanilate (PMDU), a $C_1$–$C_6$ dialkyl 4,4'-methylene-3,3'-dicarbanilate, a $C_1$–$C_6$ dialkyl 2,4'-methylene-3,3'-dicarbanilate, a $C_1$–$C_6$ dialkyl 2,2'-methylene-3,3'-dicarbanilate, a $C_1$–$C_6$ dialkyl 1,2-phenyldicarbamate, a $C_1$–$C_6$ dialkyl 1,3-phenyldicarbamate, a $C_1$–$C_6$ dialkyl 1,4-phenyldicarbamate, a $C_1$–$C_6$ dialkyl 2,4-toluenedicarbamate, a $C_1$–$C_6$ dialkyl 2,6-toluenedicarbamate, a $C_1$–$C_6$ dialkyl 1,6-naphthalenedicarbamate, a urethane corresponding to MXDI, and a urethane corresponding to TMXDI.

18. The method according to claim 1, wherein the aromatic urethane is at least one selected from the group consisting of a dialkyl 4,4'-($C_1$ to $C_4$)alkanedicarbanilate, a dialkyl 2,4'-($C_1$ to $C_4$)alkanedicarbanilate, and a dialkyl 2,2'-($C_1$ to $C_4$)alkanedicarbanilate.

19. The method according to claim 12, wherein the hydrogenated aromatic urethane is a dibutyl 4,4'-methylenedicarbanilate.

20. The method according to claim 1, wherein the hydrogenated aromatic urethane has a trans-trans isomer content of <30% and is synthesized from a bridged binuclear starting product.

21. The method according to claim 1, wherein the hydrogenated aromatic urethane has a trans-trans isomer content of 5 to 15% and is synthesized from a bridged binuclear starting product.

22. The method according to claim 1, wherein dibutyl 4,4'-methylenedicarbanilate is hydrogenated to form dibutyl 4,4'-methylenedicyclohexylcarbamate having a trans-trans isomer content of <30%.

23. The method according to claim 1, wherein dibutyl 4,4'-methylenedicarbanilate is hydrogenated to form dibutyl 4,4'-methylenedicyclohexylcarbamate having a trans-trans isomer content of 5 to 15%.

24. The method according to claim 1, wherein the hydrogenating is carried out in a solvent or solvent mixture.

25. The method according to claim 1, wherein the hydrogenating is carried out in a solvent comprising at least one of an alcohol or an ether.

26. The method according to claim 25, wherein the solvent comprises an alcohol, and the alcohol corresponds to the alcohol group of the urethane.

27. The method according to claim 25, wherein the solvent comprises n-butanol.

28. The method according to claim 25, wherein the solvent comprises tetrahydrofuran.

29. The method according to claim 1, wherein the dissociating step takes place in the gas or liquid phase, with or without catalyst, in the presence or absence of solvents, continuously or batchwise.

30. The method according to claim 1, wherein the dissociating step takes place in, combined cracking and rectification column.

31. The method according to claim 1, wherein the dissociating step takes place in liquid phase without additional solvent.

32. The method according to claim 1, wherein the dissociating step taken place in the presence of at least one catalyst.

33. The method according to claim 32, wherein the dissociating step takes place in the presence of 1 to 2,000 ppm of the catalyst, relative to the volume of the mixture in a cracking reactor.

34. The method according to claim 33, wherein the cracking reactor comprises a cracking column including a bottom, and dissociating further comprises drawing off one or more secondary products from the bottom of the cracking column.

35. The method according to claim 33, wherein the cracking reactor comprises a combined cracking and rectification column, and dissociating further comprises purifying a raw isocyanate drawn off from the combined cracking and rectification column by vacuum distillation, and wherein one or more first runnings and distillation residues may be recycled to the combined cracking and rectification column.

36. The method according to claim 1, wherein the dissociating step takes place at a temperature of 200 to 300° C.

37. The method according to claim 1, further comprising pre-purifying before dissociating, wherein the solvents are first separated by nitrogen stripping and then the concentrations of further secondary components are reduced by means of a two-stage combination of short-path evaporation and thin-film evaporation.

38. The method according to claim 1, wherein the method is carried out completely continuously, semi-continuously or in batches.

39. The method according to claim 1, wherein the aromatic isocyanate is bis{4-isocyanatophenyl}methane (MDI), the aliphatic isocyanate is bis{4-isocyanatocyclohexyl}methane ($H_{12}$MDI) with a trans-trans isomer content of <30%, and the method comprises:

i. urethanizing the MDI to form dialkyl 4,4'-methylenedicarbanilate (MDU), ii. hydrogenating the MDU to form a hydrogenated MDU, and iii. dissociating the hydrogenated MDU to form $H_{12}$MDI.

40. The method according to claim 1, wherein dissociating the hydrogenated urethane forms a cycloaliphatic isocyanate.

41. The method according to claim 1, wherein the aromatic isocyanate is at least one selected from the group consisting of a compound of formula I, formula II, formula III, formula IV, formula V, formula VI, formula VII, and formula VIII:

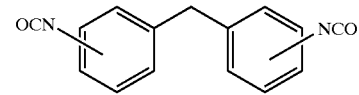

I

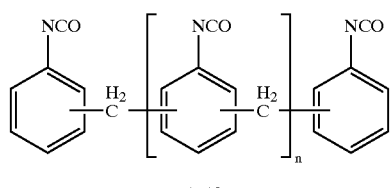

II n = 1–10,

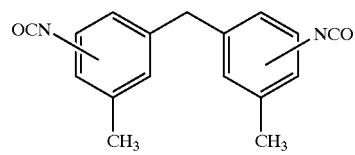

III

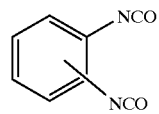

IV

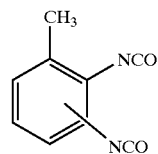

V

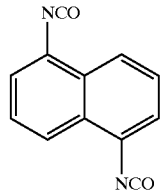

VI

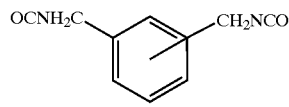

VII

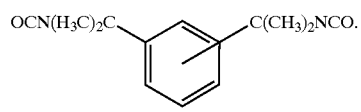

VIII

42. The method according to claim 17, wherein the aromatic urethane is at least one selected from the group consisting of a compound of formula I, formula II, formula III, formula IV, formula V, formula VI, formula VII and formula VIII:

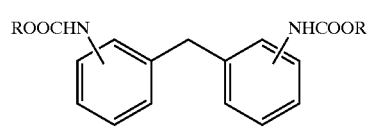

I

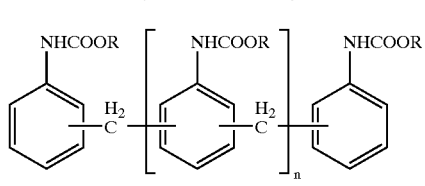

II n = 1–10,

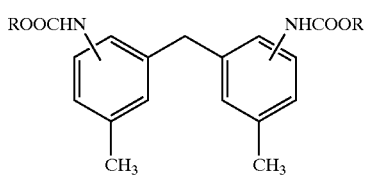

III

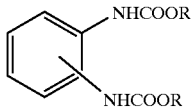

IV

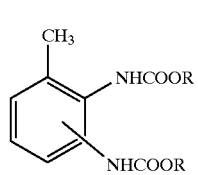

V

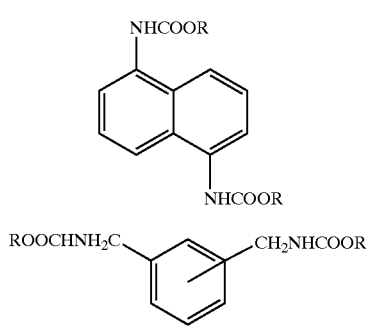
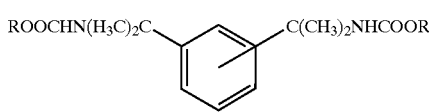
wherein R is $C_1$–$C_6$ alkyl group.
43. The method according to claim 1, wherein the urethanizing step is carried out at temperatures of 20° C. to 120° C.
44. The method according to claim 1, wherein the catalyst support has a BET surface area from 32 $m^2$/g to less than 70 $m^2$/g.
* * * * *